(12) United States Patent
Horner et al.

(10) Patent No.: US 11,185,363 B2
(45) Date of Patent: *Nov. 30, 2021

(54) FILTER CONNECTION FOR A SMOKE EVACUATION DEVICE

(71) Applicant: Megadyne Medical Products, Inc., Draper, UT (US)

(72) Inventors: Shawn K. Horner, Woods Cross, UT (US); Steven D. Andrews, West Jordan, UT (US); David Yates, West Chester, OH (US)

(73) Assignee: Megadyne Medical Products, Inc., Draper, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/825,998

(22) Filed: Mar. 20, 2020

(65) Prior Publication Data

US 2020/0214760 A1    Jul. 9, 2020

Related U.S. Application Data

(63) Continuation of application No. 15/826,325, filed on Nov. 29, 2017, now Pat. No. 10,631,916.

(51) Int. Cl.
*B01D 46/00* (2006.01)
*H01R 13/00* (2006.01)
(Continued)

(52) U.S. Cl.
CPC .......... *A61B 18/14* (2013.01); *B01D 46/0005* (2013.01); *B01D 46/0012* (2013.01);
(Continued)

(58) Field of Classification Search
CPC ......... B01D 46/00; B01D 46/24; F04B 39/06; A61B 18/14; A61B 18/00; A61B 18/12; F24F 3/16; H01R 13/00
(Continued)

(56) References Cited

U.S. PATENT DOCUMENTS 1,165,288 A    12/1915   Rimmer
1,789,194 A    1/1931    Rockwell
(Continued)

FOREIGN PATENT DOCUMENTS

WO    9408698    4/1994
WO    2016142690    9/2016
(Continued)

OTHER PUBLICATIONS

Bovie 35 hour filter found online [Sep. 11, 2018]—http://www.boviemedical.com/smoke-shark-ii/.
(Continued)

*Primary Examiner* — Minh Chau T Pham
(74) *Attorney, Agent, or Firm* — Workman Nydegger

(57) ABSTRACT

A filter connection for a smoke evacuation device includes a filter canister assembly and a socket. The filter canister assembly has a cross-sectional shape with only one line of symmetry that corresponds to a cross-sectional shape of the socket so that the filter canister can only be inserted into the socket in one orientation. One or more key notches on the filter canister may also ensure that the filter is properly installed. A seal creates an airtight boundary between the filter canister and a recess of the socket so that a sealed path in communication with the smoke evacuation device is established before the filter canister is fully inserted into the socket. An electronic connection is made between the filter canister and the socket after the airtight boundary is created.

20 Claims, 9 Drawing Sheets

(51) Int. Cl.
  *A61B 18/14* (2006.01)
  *B01D 46/24* (2006.01)
  *F24F 8/10* (2021.01)
  *A61B 18/00* (2006.01)
  *A61B 18/12* (2006.01)

(52) U.S. Cl.
  CPC ........ *B01D 46/0043* (2013.01); *B01D 46/24* (2013.01); *F24F 8/10* (2021.01); *H01R 13/005* (2013.01); *A61B 18/1206* (2013.01); *A61B 2018/00178* (2013.01); *A61B 2018/00595* (2013.01); *A61B 2018/00601* (2013.01); *A61B 2218/008* (2013.01); *B01D 2265/026* (2013.01); *B01D 2271/027* (2013.01); *B01D 2279/35* (2013.01)

(58) Field of Classification Search
  USPC .............. 55/385.1, 471; 96/380, 407, 418; 604/19–27, 319
  See application file for complete search history.

(56) References Cited

U.S. PATENT DOCUMENTS

| | | |
|---|---|---|
| 2,577,606 A | 12/1951 | Conley |
| 3,815,752 A | 6/1974 | Hoffman et al. |
| 3,841,490 A | 10/1974 | Hoffman et al. |
| 4,157,234 A | 6/1979 | Shaffer et al. |
| 4,396,206 A | 8/1983 | Tsuge et al. |
| 4,619,672 A | 10/1986 | Robertson |
| 4,701,193 A * | 10/1987 | Robertson ............ A61M 1/0066 55/385.1 |
| 4,786,298 A | 11/1988 | Billet et al. |
| 4,810,269 A | 3/1989 | Stackhouse et al. |
| 4,826,513 A | 5/1989 | Stackhouse et al. |
| 4,986,839 A | 1/1991 | Wertz et al. |
| 5,108,389 A | 4/1992 | Comescu |
| 5,144,176 A | 9/1992 | Popper |
| 5,160,334 A | 11/1992 | Billings et al. |
| 5,221,192 A | 6/1993 | Heflin et al. |
| 5,226,939 A | 7/1993 | Nicolas et al. |
| 5,242,474 A | 9/1993 | Herbst et al. |
| 5,288,469 A | 2/1994 | Skalla et al. |
| 5,318,516 A | 6/1994 | Comescu |
| 5,336,218 A | 8/1994 | Linhares |
| 5,342,349 A | 8/1994 | Kaufman |
| 5,423,779 A | 6/1995 | Yeh |
| 5,431,650 A | 7/1995 | Comescu |
| 5,456,248 A | 10/1995 | Holian |
| 5,522,808 A | 6/1996 | Skalla |
| 5,597,385 A | 1/1997 | Moerke |
| 5,620,441 A | 4/1997 | Greff et al. |
| 5,674,219 A | 10/1997 | Monson et al. |
| 5,690,480 A | 11/1997 | Suzuki et al. |
| 5,853,410 A | 12/1998 | Greff et al. |
| 5,874,052 A | 2/1999 | Holland |
| 5,910,291 A | 6/1999 | Skalla et al. |
| 5,992,413 A | 11/1999 | Martin et al. |
| 6,050,792 A | 4/2000 | Shaffer |
| 6,110,259 A | 8/2000 | Schultz et al. |
| 6,129,530 A | 10/2000 | Shaffer |
| 6,203,590 B1 | 3/2001 | Byrd |
| 6,203,762 B1 | 3/2001 | Skalla et al. |
| 6,439,864 B1 | 8/2002 | Shaffer |
| D467,654 S | 12/2002 | Klug et al. |
| 6,511,308 B2 | 1/2003 | Shaffer |
| 6,524,307 B1 | 2/2003 | Palmerton et al. |
| 6,544,210 B1 | 4/2003 | Trudel et al. |
| 6,585,791 B1 | 7/2003 | Garito et al. |
| 6,589,316 B1 | 7/2003 | Schultz et al. |
| 6,592,543 B1 | 7/2003 | Wortrich et al. |
| 6,616,722 B1 | 9/2003 | Cartellone |
| 6,663,698 B2 | 12/2003 | Mishin et al. |
| D485,339 S | 1/2004 | Klug |
| 6,709,248 B2 | 3/2004 | Fujioka et al. |
| 6,736,620 B2 | 5/2004 | Satoh |
| 6,758,885 B2 | 7/2004 | Leffel et al. |
| 6,786,707 B2 | 9/2004 | Kim |
| D513,314 S | 12/2005 | Iddings |
| 7,014,434 B2 | 3/2006 | Fujioka et al. |
| D521,137 S | 5/2006 | Khalil |
| D545,955 S | 7/2007 | Arlas |
| 7,258,712 B2 | 8/2007 | Schultz et al. |
| 7,276,052 B2 | 10/2007 | Kobayashi et al. |
| D555,803 S | 11/2007 | Galrto |
| 7,294,116 B1 | 11/2007 | Ellman et al. |
| 7,465,156 B2 | 12/2008 | Lee |
| 7,497,340 B2 | 3/2009 | Hershberger et al. |
| 7,597,731 B2 | 10/2009 | Palmerton |
| D625,399 S | 10/2010 | Horiguchi |
| D626,204 S | 10/2010 | Morgan |
| 7,819,957 B2 | 10/2010 | Roberts et al. |
| 7,942,655 B2 | 5/2011 | Shaffer |
| D646,368 S | 10/2011 | Osendorf et al. |
| 8,033,798 B2 | 10/2011 | Suh et al. |
| D648,841 S | 11/2011 | Lam |
| 8,142,175 B2 | 3/2012 | Duppert et al. |
| 8,190,398 B2 | 5/2012 | Kitaguchi et al. |
| D666,704 S | 9/2012 | Osendorf |
| 8,298,420 B2 | 10/2012 | Burrows |
| 8,608,816 B2 | 12/2013 | Palmerton et al. |
| 8,684,705 B2 | 4/2014 | Magoon et al. |
| 8,727,744 B2 | 5/2014 | Magoon et al. |
| 9,011,366 B2 | 4/2015 | Dean et al. |
| 9,028,230 B2 | 5/2015 | Shaffer |
| 9,067,030 B2 | 6/2015 | Stearns et al. |
| 9,074,598 B2 | 7/2015 | Shaffer et al. |
| 9,199,047 B2 | 12/2015 | Stearns et al. |
| 9,215,964 B2 | 12/2015 | Loske |
| 9,366,254 B2 | 6/2016 | Murakami |
| 9,387,295 B1 | 7/2016 | Mastri et al. |
| 9,387,296 B1 | 7/2016 | Mastri et al. |
| D764,649 S | 8/2016 | Ko |
| 9,415,160 B2 | 8/2016 | Bonano et al. |
| 9,435,339 B2 | 9/2016 | Calhoun et al. |
| 9,474,512 B2 | 10/2016 | Blackhurst et al. |
| 9,532,843 B2 | 1/2017 | Palmerton |
| 9,549,849 B2 | 1/2017 | Charles |
| 9,579,428 B1 | 2/2017 | Reasoner et al. |
| D802,024 S | 11/2017 | Aoki |
| 9,867,914 B2 | 1/2018 | Bonano et al. |
| 9,943,355 B2 | 4/2018 | Babini et al. |
| 10,631,916 B2 * | 4/2020 | Horner ............... B01D 46/0005 |
| D886,976 S | 6/2020 | Horner et al. |
| D890,900 S | 7/2020 | Bink et al. |
| D912,762 S | 3/2021 | Horner et al. |
| 2004/0223859 A1 | 11/2004 | Sharp |
| 2005/0000196 A1 | 1/2005 | Schultz |
| 2005/0189283 A1 | 9/2005 | Smit et al. |
| 2006/0099096 A1 | 5/2006 | Shaffer et al. |
| 2007/0066970 A1 | 3/2007 | Ineson |
| 2009/0022613 A1 | 1/2009 | Dai et al. |
| 2013/0231606 A1 | 9/2013 | Stearns et al. |
| 2014/0356207 A1 | 12/2014 | Yang |
| 2015/0224237 A1 | 8/2015 | Reasoner et al. |
| 2015/0273381 A1 | 10/2015 | Stoner et al. |
| 2016/0000494 A1 | 1/2016 | Comescu |
| 2016/0001102 A1 | 1/2016 | Huh |
| 2016/0287817 A1 | 10/2016 | Mastri et al. |
| 2016/0367266 A1 | 12/2016 | Palmerton et al. |
| 2017/0014557 A1 | 1/2017 | Minskoff et al. |
| 2017/0014560 A1 | 1/2017 | Minskoff et al. |
| 2017/0165725 A1 | 6/2017 | Hersey et al. |
| 2017/0181768 A1 | 6/2017 | Galley |
| 2019/0159827 A1 | 5/2019 | Horner et al. |
| 2019/0159830 A1 | 5/2019 | Horner et al. |

FOREIGN PATENT DOCUMENTS

| | | |
|---|---|---|
| WO | 201703712 | 1/2017 |
| WO | 2017112684 | 6/2017 |

(56) References Cited

FOREIGN PATENT DOCUMENTS

OTHER PUBLICATIONS

"Megadyne Surgical Smoke Evacuation System found online [Sep. 11, 2018]—http://www.hcp-austria.com/Minivac%20Smoke%20Evacuators.html".
Non-Final Office Action for U.S. Appl. No. 29/627,793 dated Oct. 29, 2018.
Notice of Allowance for U.S. Appl. No. 15/826,325 dated Dec. 26, 2019.
Non-Final Office Action for U.S. Appl. No. 15/826,325 dated Aug. 1, 2019.
Notice of Allowance for U.S. Appl. No. 29/627,793 dated Feb. 21, 2020.
U.S. Appl. No. 29/627,793, filed Nov. 29, 2017.
Notice of Allowance received for U.S. Appl. No. 29/733,877, dated Sep. 2, 2021, 9 pages.

* cited by examiner

FILTER CONNECTION FOR A SMOKE EVACUATION DEVICE

CROSS-REFERENCE TO RELATED APPLICATIONS

This application is a continuation application of U.S. patent application Ser. No. 15/826,325, filed Nov. 29, 2017, and entitled Filter Connection for a Smoke Evacuation Device, now U.S. Pat. No. 10,631,916, the entire content of which is incorporated herein by reference.

BACKGROUND

1. Technical Field

The present disclosure relates to smoke evacuation systems used in electrosurgical systems. More specifically, the present disclosure relates to apparatus and methods of connecting filters in smoke evacuation systems.

2. The Relevant Technology

As is known to those skilled in the art, modern surgical techniques typically employ radio frequency (RF) power to cut tissue and coagulate bleeding encountered in performing surgical procedures. Such electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue through cauterization. The return electrode carries the same RF signal provided to the electrode or tip of the electrosurgical instrument, after it passes through the patient, thus providing a path back to the electrosurgical generator.

Electrosurgical instruments communicate electrical energy to a target tissue of a patient to cut the tissue and/or cauterize blood vessels within and/or near the target tissue. This cutting and cauterization result in smoke released into the air that can be unpleasant and/or obstructive of the view of a practitioner. Many electrosurgical systems may therefore employ a smoke evacuation system that captures the resulting smoke and directs it through a filter and exhaust port, away from practitioners and/or patients.

Smoke evacuation systems typically comprise a pump and a filter. The pump creates suction that draws smoke through a vacuum tube into the filter. A vacuum tube may terminate at the hand piece that includes the electrode tip so that the smoke is sucked in at the hand piece. Other electrosurgical systems may include separate hand pieces that are used to suck the smoke into the system. The smoke travels to the filter via a vacuum tube and offensive smells are filtered out as the smoke moves through the filter. Filtered air may then exit the smoke evacuation system as exhaust.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to smoke evacuation systems. More specifically, the present disclosure relates to a filter connection for a smoke evacuation device. It may be difficult to determine when filters need to be replaced in smoke evacuation systems, and current filter connections can lead to faulty installations. The filter connection of the present disclosure may enable easy installation of filters, as well as other features to electronically detect and communicate when filters need to be replaced or when an incorrect filter has been installed.

In one embodiment, a filter connection for a smoke evacuation system includes a filter canister and a socket. The filter canister comprises first and second ends, a body extending between the first and second ends, a connection nipple, a seal disposed around the connection nipple, and a first electronic connector. The socket comprises a first recess configured to receive the canister body, a second recess configured to receive the connection nipple, and a second electronic connector. The longitudinal distance between the seal and the first electronic connector is greater than the longitudinal distance between the second recess of the socket and the second electronic connector.

In one embodiment, a filter canister for a smoke evacuation system includes a first end having an inlet port, a second end, an electronic connector, and a connection nipple disposed at the second end. The cross-sectional shape of the second end of the filter canister has only one line of symmetry. The electronic connector is disposed at the second end of the filter canister.

In one embodiment, a method for connecting a filter in a smoke evacuation system includes the following steps: providing a filter canister; providing a socket in the smoke evacuation system; inserting the filter canister a first distance into the socket so that the filter canister creates an airtight boundary between the filter canister and the socket; and inserting the filter canister a second distance into the socket so that an electronic connection is made between the filter canister and the socket. The second distance is greater than the first distance.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present disclosure relates to smoke evacuation systems. More specifically, the present disclosure relates to a filter connection for a smoke evacuation device. It may be difficult to determine when filters need to be replaced in smoke evacuation systems, and current filter connections can lead to faulty installations. The filter connection of the present disclosure may enable easy installation of filters, as well as other features to electronically detect and communicate when filters need to be replaced or when an incorrect filter has been installed.

Figure 1:
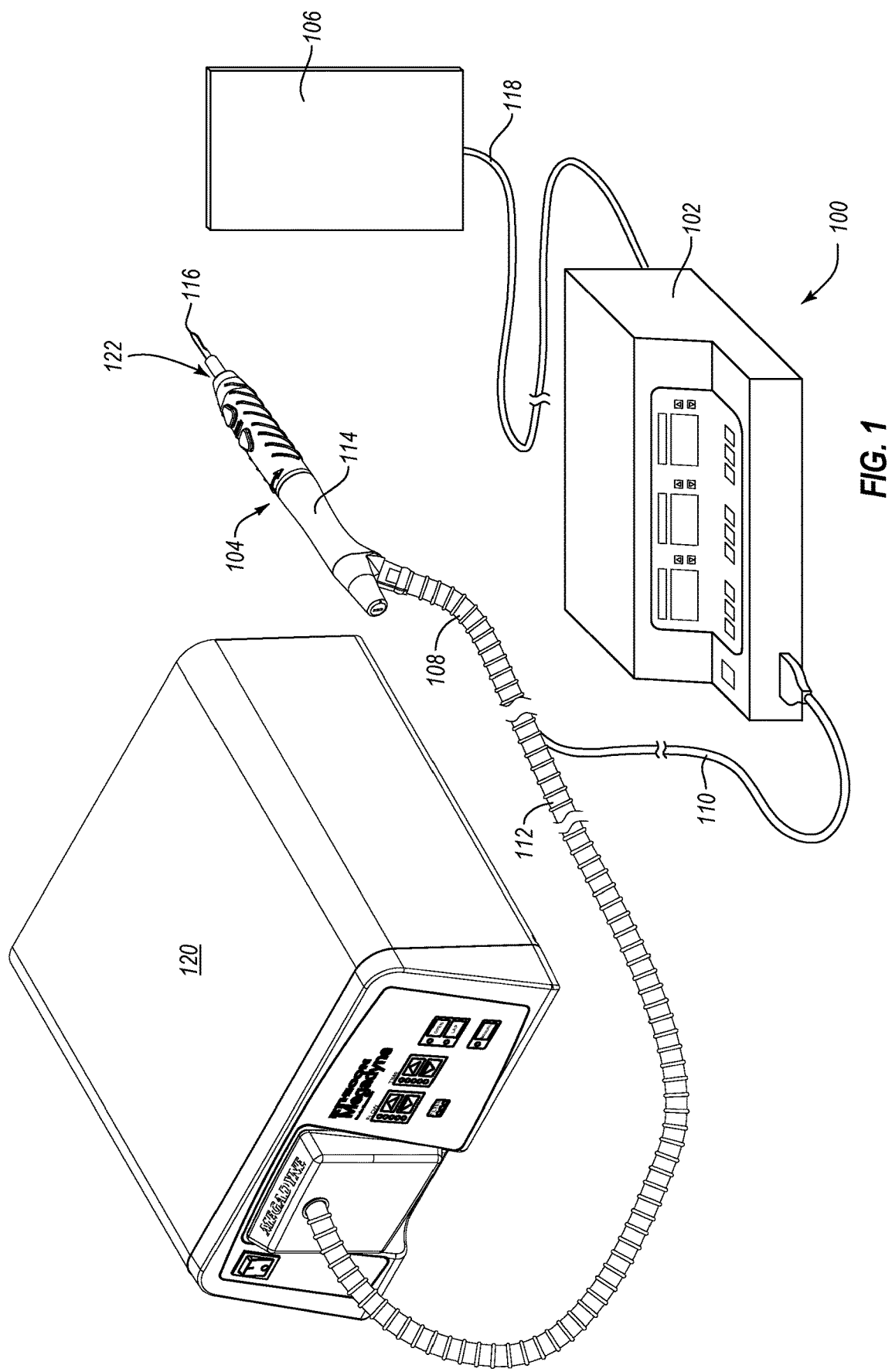
FIG. 1 illustrates an exemplary electrosurgical system.

FIG. 1 illustrates an exemplary electrosurgical system 100. The illustrated embodiment includes a signal generator 102, an electrosurgical instrument 104, a return electrode 106, and a smoke evacuation system 120. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site.

Generally, electrosurgical instrument 104 includes a hand piece or pencil 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with or adjacent to electrode tip 116. The tissue heating takes place at an appropriately high temperature to allow electrosurgical instrument 104 to be used to perform electrosurgery. Return electrode 106 is connected to generator 102 by a cable 118, and is either applied to or placed in close proximity to the patient (depending on the type of return electrode), in order to complete the circuit and provide a return electrical path to wave generator 102 for energy that passes into the patient's body.

The heating of cellular matter of the patient by the electrode tip 116, or cauterization of blood vessels to prevent bleeding, results in smoke being released where the cauterization takes place. The electrosurgical instrument 104 may comprise a smoke evacuation conduit opening 122 near the electrode tip 116 so as to be able to capture the smoke that is released during a procedure. Vacuum suction may draw the smoke into the conduit opening 122, through the electrosurgical instrument 104, and into the vacuum hose 112 toward the smoke evacuation system 120.

Figure 2:
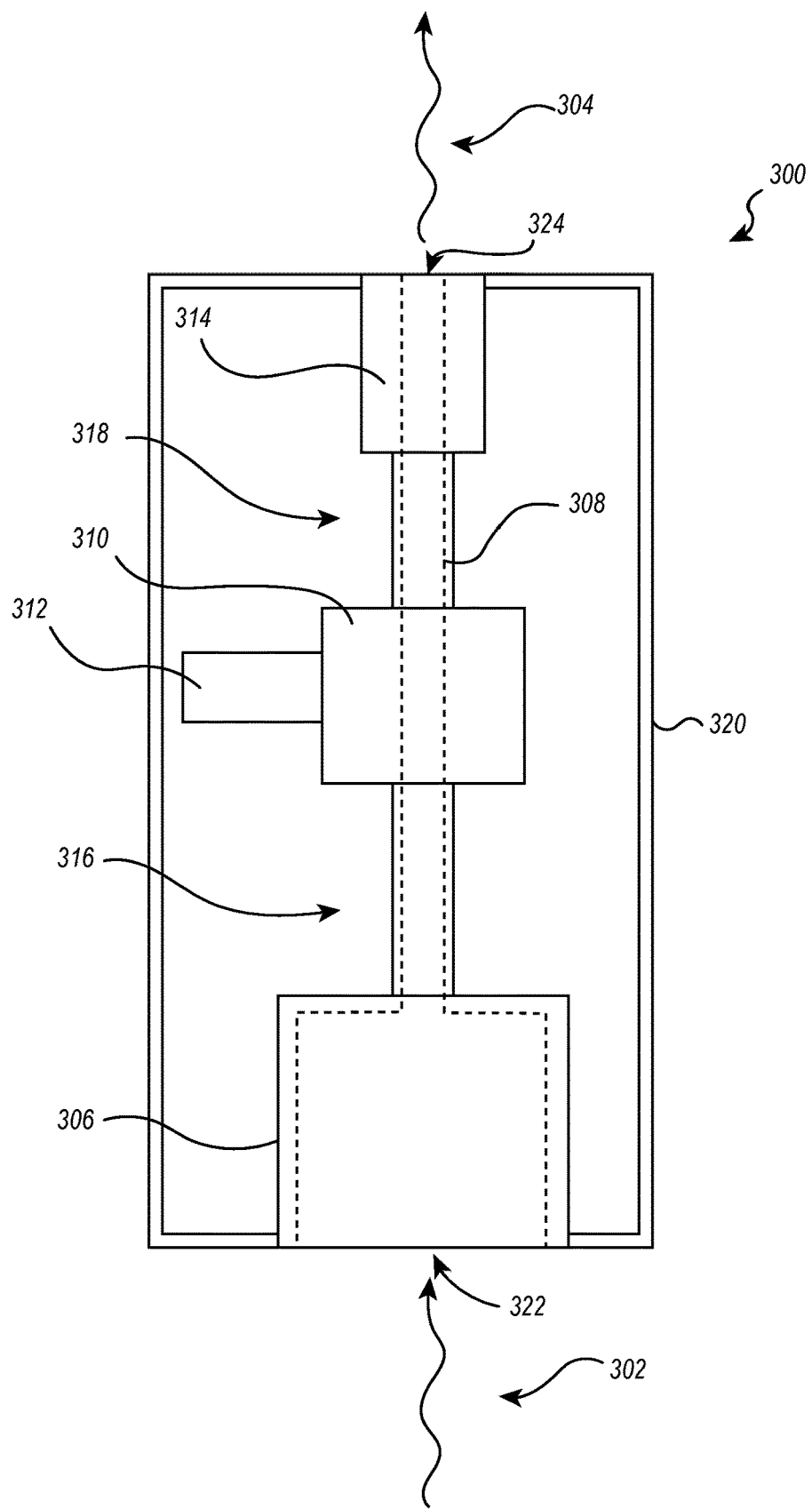
FIG. 2 illustrates a schematic of an embodiment of a smoke evacuation system.

FIG. 2 illustrates an embodiment of a smoke evacuation system 300. The smoke evacuation system 300 may include a filter 306 and an airflow path 308. The airflow path 308 may comprise a pump 310 disposed in-line with the airflow path 308 producing a pressure difference within the airflow path 308 by mechanical action. This pressure difference may cause movement of a gas through the airflow path 308. The gas drawn through the airflow path 308 may be smoke 302, or the filtered air remaining after the smoke 302 has passed through the filter 306. A motor 312 drives the pump 310.

The smoke evacuation system 300 may also include an exhaust mechanism 314 that may also be disposed in-line with the airflow path 308. The exhaust mechanism 314 may be a mechanism that controls the velocity, direction, and/or other properties of the filtered gas 304 exiting the smoke evacuation system 300 at the outlet port 324.

The airflow path 308 may be disposed between an inlet port 322 and an outlet port 324. The smoke 302 may flow into the filter 306 at the inlet port 322, be pumped through the airflow path 308 by the pump 310 so that the smoke 302 is drawn through the filter 306, through the exhaust mechanism 314, and out the outlet port 324 of the smoke evacuation system 300. The air exiting the smoke evacuation system 300 at the outlet port 324 may be the exhaust 304. The exhaust 304 may consist of filtered air/gas that has passed through the smoke evacuation system 300 and exits through the outlet port 324.

The airflow path 308 may comprise a first zone 316 and a second zone 318. The first zone 316 may be upstream from the pump 306 and the second zone 318 may be downstream from the pump 306. The pump 306 may pressurize the air in the airflow path 308 so that the air in the second zone 318 has a higher pressure than the air in the first zone 316.

The smoke evacuation system 300 may also include a housing 320. FIG. 2 illustrates a cross-sectional view of a smoke evacuation system 300 to show the various components within the housing 320. The housing 320 may completely or partially encompass the smoke evacuation system 300. The airflow path 308 may be at least partially comprised of a tube or other conduit that substantially contains and/or isolates the air moving through the airflow path 308 from air outside the airflow path 308.

For example, the first zone 316 of the airflow path 308 may comprise a tube through which the airflow path 308 extends between the filter 306 and the pump 310. The second zone 318 of the airflow path 308 may also comprise a tube through which the airflow path 308 extends between the pump 310 and the exhaust mechanism 314. The airflow path 308 also extends through the filter 306, pump 310, and exhaust mechanism 314 so that a continuous airflow path 308 extends from the inlet port 322 to the outlet port 324.

Figure 3A:
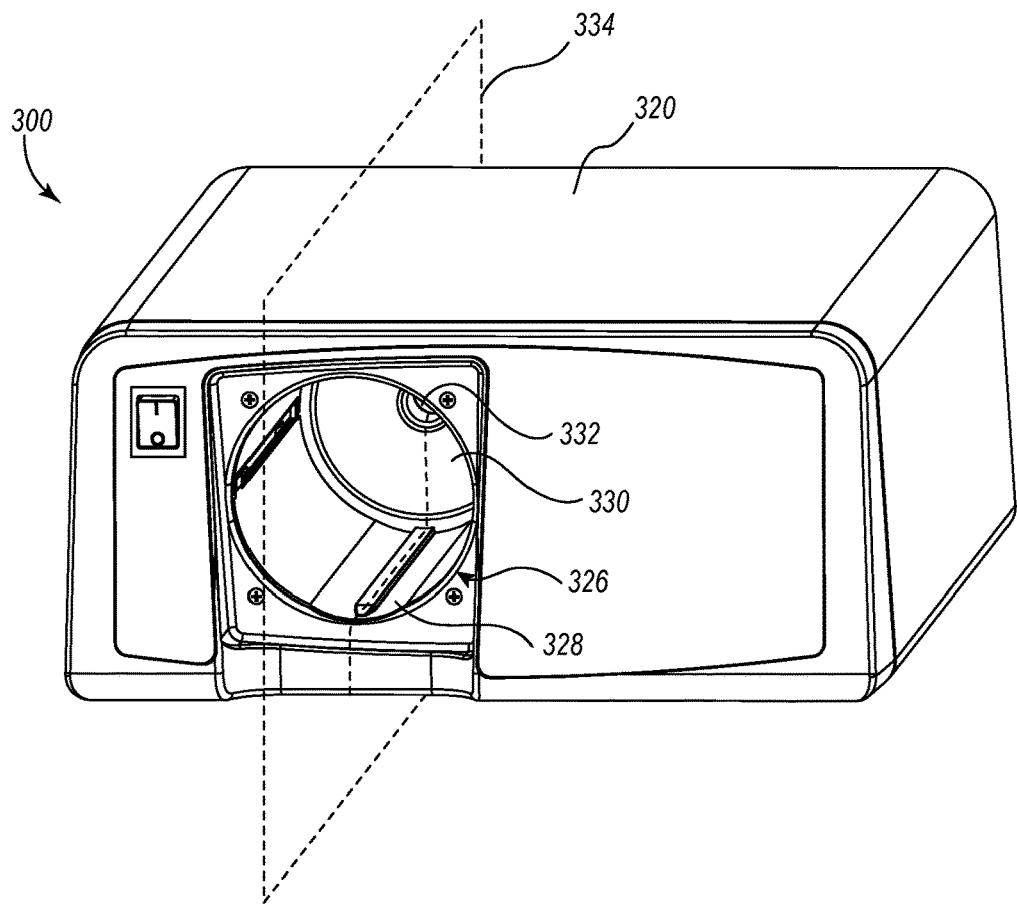
FIG. 3A illustrates a perspective view of an embodiment of a smoke evacuation system.

FIG. 3A illustrates a perspective view of a smoke evacuation system 300. The smoke evacuation system 300 may include a socket 326 configured to receive a filter 306. The filter 306 is not shown in FIG. 3A in order to illustrate the socket 326. The socket 326 may have a first recess 328 and a second recess 332. A transition surface 330 extends between the first recess 328 and the second recess 332. The socket 326 may be shaped to receive a filter 306 into the socket so that the filter 306 fits snuggly into the socket 326.

Figure 3B:
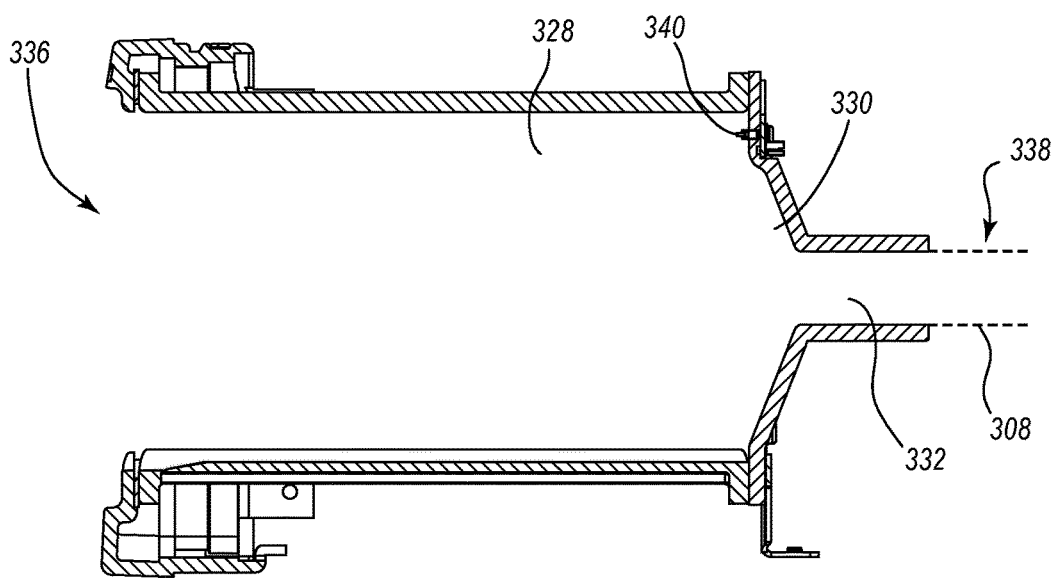
FIG. 3B illustrates a cross-sectional view of the system illustrated in FIG. 3A, wherein an embodiment of a socket is shown.

FIG. 3B illustrates a cross-sectional view of the smoke evacuation system 300 of FIG. 3A. FIG. 3B illustrates a cross-sectional view of plane 334 illustrated in FIG. 3A that passes through the socket 326. As shown in FIG. 3B, the socket comprises a first end 336 that is open to receive a filter 306 and a second end 338 in communication with the airflow path 308. A filter 306 may be inserted and removed from the first end 336 of the socket 326.

The socket 326 may also include a transition surface 330 configured to receive a second end of a filter canister assembly, a second recess 332 configured to receive a connection nipple, and an electronic connector 340. More details regarding filter canister assembly, including the body, second end, connection nipple, and electronic connector will be given hereafter.

Figure 4A:
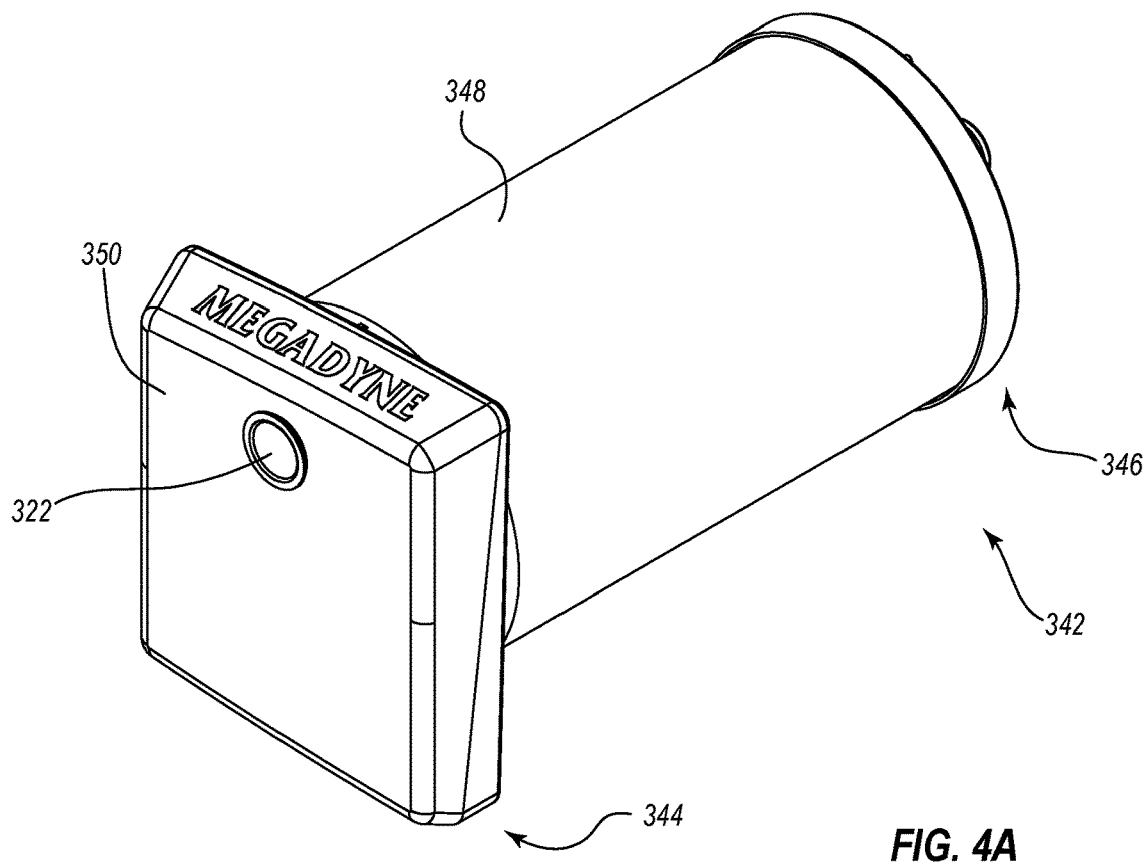
FIG. 4A illustrates a perspective view of an embodiment of a filter canister assembly.
Figure 4B:
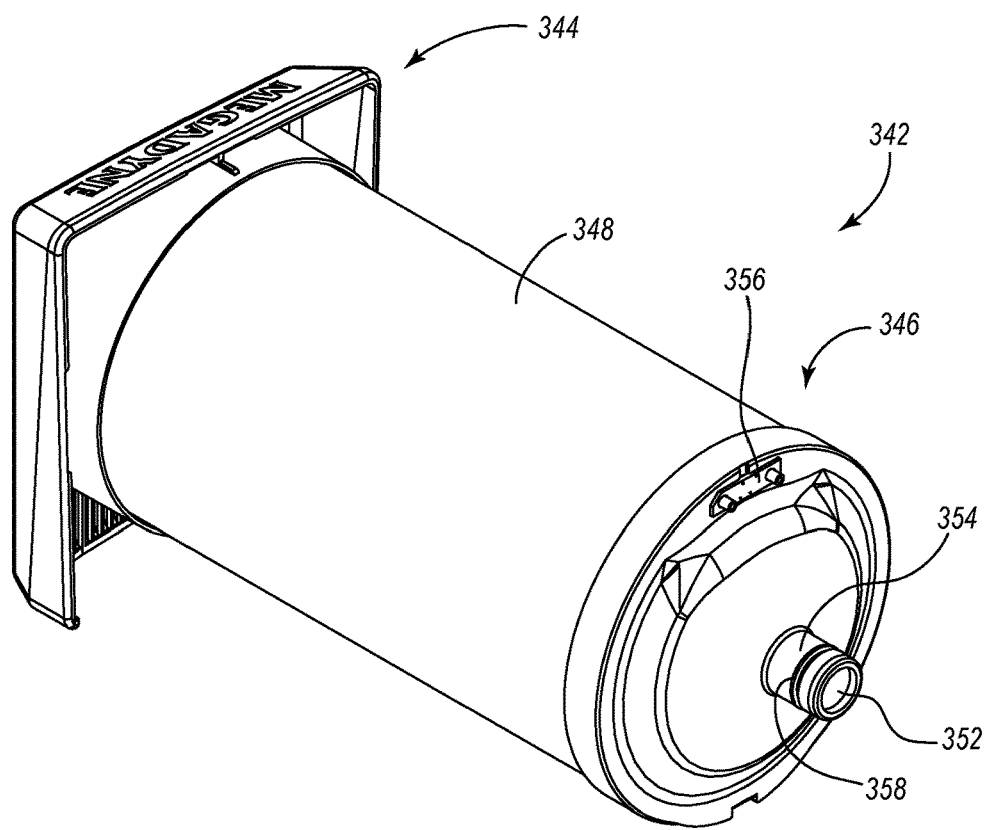
FIG. 4B illustrates a perspective view of an embodiment of a filter canister assembly.

FIGS. 4A through 4B illustrate various views of an embodiment of a filter canister assembly 342. FIG. 4A illustrates a perspective view of the filter canister assembly 342. The filter canister assembly 342 may include a first end 344 and a second end 346. The second end 346 of the filter canister 342 may be at least partially conical. A canister body 348 may be disposed between the first end 344 and the second end 346 of the canister assembly 342. The filter canister assembly 342 may be configured to be inserted into the socket 326 of the smoke evacuation system 300.

A plate 350 may be disposed on the first end 344 of the canister assembly 342 so that the canister assembly 342 may not be inserted too far into the socket 326. When the canister assembly 342 has been fully inserted into the socket 326, the plate 350 makes contact with the outer housing 320 and/or the second end 346 of the canister assembly 342 abuts the transition surface 330 of the socket 326 so that the canister assembly 342 may not be inserted further. The second end 346 and the body 348 of the canister assembly 342 may be able to fit into the socket 326, but the plate 350 may not. The canister assembly 342 may be inserted until the plate 350 comes into contact with the outer housing 320 of the smoke evacuation system 300. The plate 350 may include an inlet port 322 such as the inlet port 322 discussed above with reference to FIG. 2. The vacuum hose 112 illustrated in FIG. 1 may connect to the inlet port 322 so that smoke may travel through the vacuum hose 112 and into the filter canister assembly 342 at the inlet port 322.

Smoke may enter at the inlet port 322 and move through an inner pathway of the filter 306 disposed within the body 348 of the filter canister assembly 342. Potentially harmful and/or unpleasant toxins and particulates may become trapped in the filter 306 as the smoke moves through the filter 306. The filtered gas remaining after filtration may exit the filter canister assembly 342 through the canister outlet 352 illustrated in FIG. 4B. The filter canister assembly 342 may be inserted into the socket 326 of the smoke evacuation system 300 so that the canister outlet 352 communicates with the airflow path 308.

FIG. 4B illustrates a perspective view of the second end 346 of the filter canister assembly 342. The second end 346 may include a connection nipple 354 surrounding the canister outlet 352 and a first electronic connector 356. In one embodiment, the first electronic connector may be an erasable programmable read-only memory (EPROM) connector. The first electronic programmable connector 356 may be a male connector. Other embodiments may include a first electronic programmable connector that is a female connector. The second end 346 of the canister assembly 342 may also include a seal 358 disposed around the connection nipple 354. More details regarding the connection nipple 354, seal 358, and electronic programmable connector 356 will be given hereafter in reference to FIG. 6A and FIG. 6B.

Figure 5B:
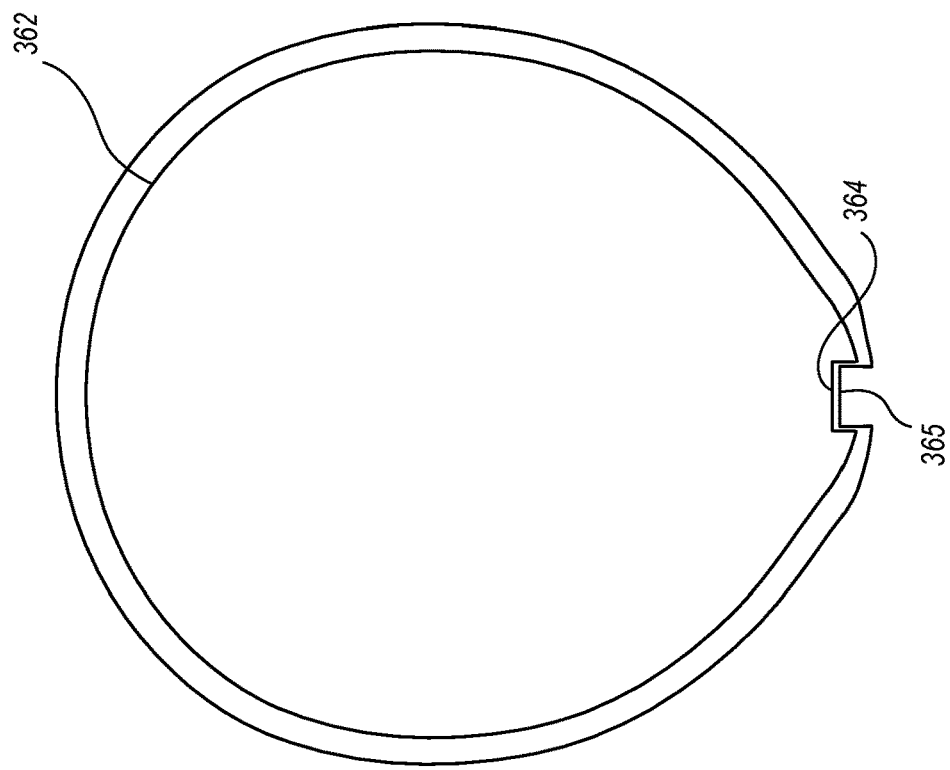
FIG. 5B illustrates a schematic of a cross-sectional shape of one end of a filter canister assembly and an opening of a socket.
Figure 5A:
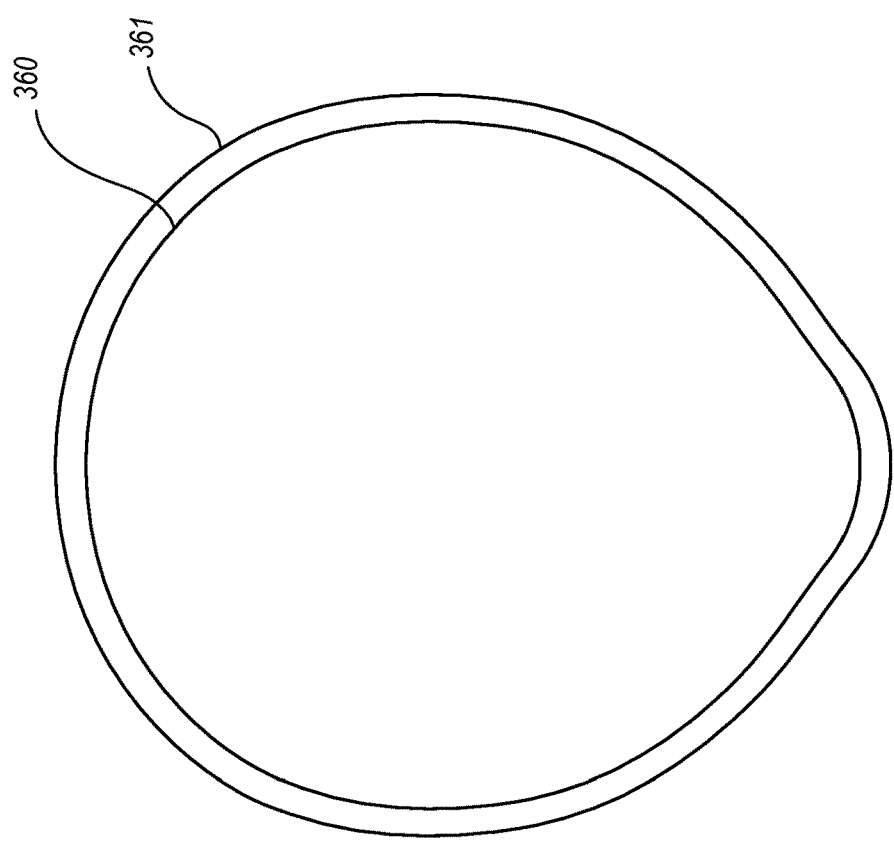
FIG. 5A illustrates a schematic of a cross-sectional shape of one end of a filter canister assembly and an opening of a socket.

FIG. 5A illustrates the cross-sectional shape of the second end of a filter canister 360 and the cross-sectional shape of the first recess of a socket 361. The cross-sectional shape of the second end of the filter canister 360 may be similar to the cross-sectional shape of the first recess of the socket 361 and only slightly smaller so that the filter canister assembly 360 may fit snuggly into the socket 361 when inserted. The cross-sectional shape of the second end of the canister assembly 360 may be slightly smaller than the cross-sectional shape of the first recess of the socket 361 so that the filter canister 360 may be inserted therein.

FIG. 5A illustrates teardrop shaped cross-sections 360, 361. A teardrop cross sectional shape 360, 361 may ensure that the filter canister 360 may only be inserted in a particular orientation so that the filter canister 360 fits into the socket 361. Other embodiments may include cross-sectional shapes that are different from the teardrop shape illustrated in FIG. 5A. Other embodiments may include any other cross-sectional shapes so long as the cross-sectional shape limits the canister assembly 360 to being inserted into the socket 361 in only one orientation.

For example, in one embodiment, the cross-sectional shape 360, 361 may be a triangle having only one line of symmetry. Other embodiments may include other cross-sectional shapes that only have one line of symmetry. Limiting the canister assembly 342 to a single orientation may assure that the filter canister 360 is inserted correctly into the socket 361.

Figure 5C:
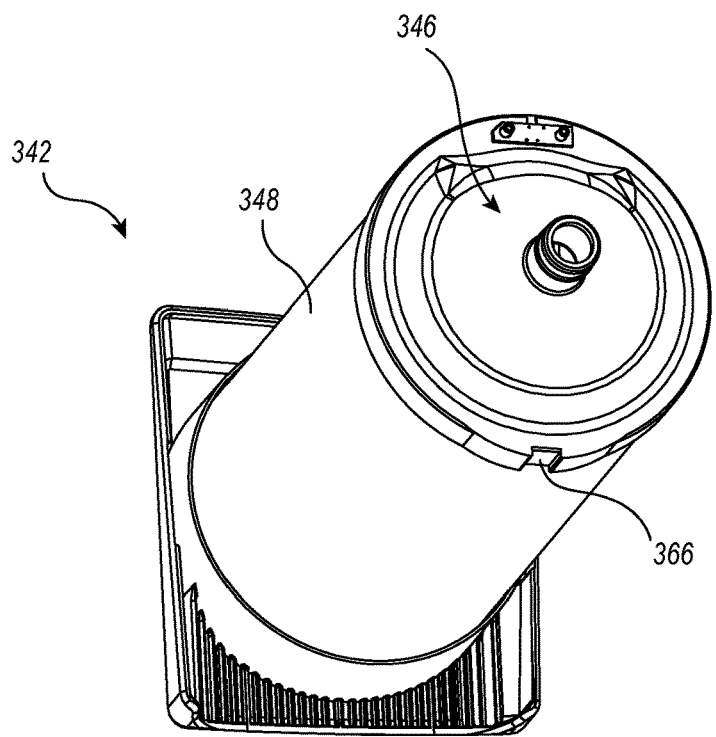
FIG. 5C illustrates a perspective view of an embodiment of a filter canister.
Figure 5D:
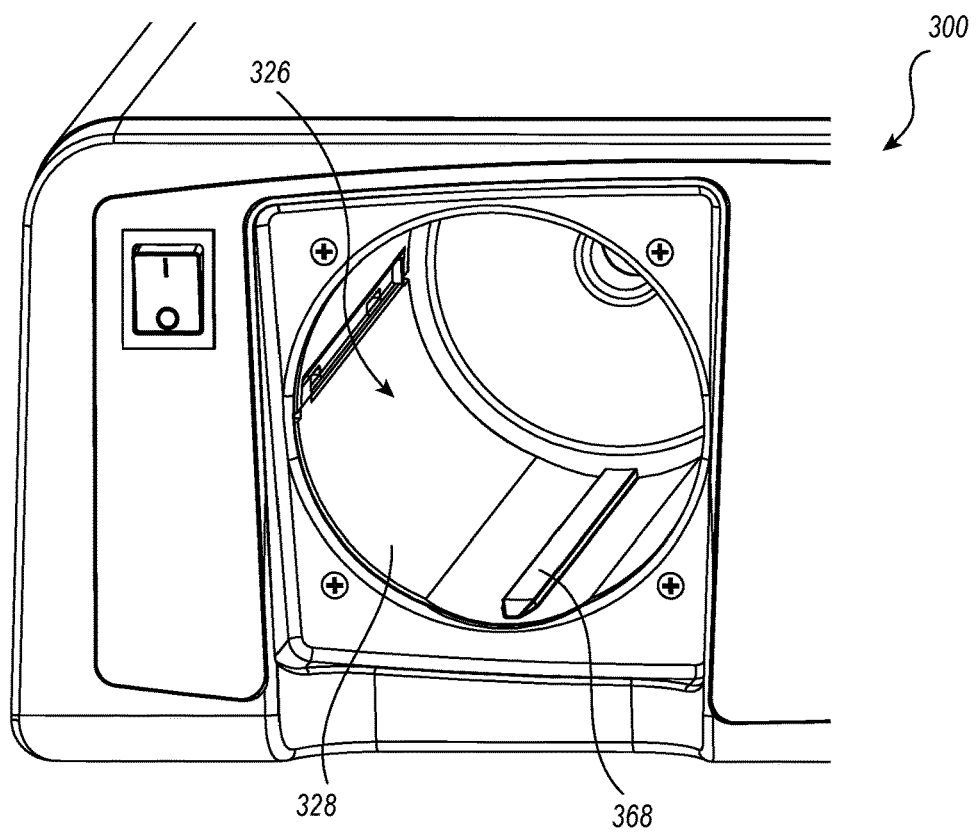
FIG. 5D illustrates a perspective view of an embodiment of a socket of a smoke evacuation system.

FIG. 5B illustrates another cross-sectional shape of a filter canister 362. The shape 362 shown in FIG. 5B is similar to the shape 360, 361 shown in FIG. 5A, except the cross-sectional shape 362 includes a key notch 364. The socket cross-sectional shape has a corresponding key groove 365. FIG. 5C illustrates a canister assembly 342 that includes a second end 346 having a cross-sectional shape 362 as shown in FIG. 5B. FIG. 5D illustrates a smoke evacuation system 300 that includes a socket 326 having a first recess 328 with a cross-sectional shape 362 as shown in FIG. 5B. The key notch 366 of the second end 346 of the canister assembly 342 must align with a key groove 368 of the first recess 328 of the socket 326 in order to be inserted. The key notch 366 and groove 368 may further assure that the canister assembly 342 is properly inserted into the socket 326. Other embodiments of shapes 360 and 362 are contemplated herein. For example, a circular or square shape with a key notch 364 may also be used.

Other embodiments may include more than one key notch 366 and groove 368 at various locations around the cross sectional shape 362 so that multiple key notches 366 and grooves 368 on the canister assembly 342 and socket 326 must be aligned before the canister assembly 342 is inserted into the socket 326. Some embodiments of a canister assembly 342 may also include a body 348 that also has a cross-sectional shape shown in FIGS. 5A and 5B and described herein so that the shape of the body 348 corresponds to the socket 326 when it is inserted.

In some embodiments, the key notch 366 may extend along the whole length of the body 348 of the canister assembly 342 and the key groove 368 may not extend along the whole length of the first recess 328 of the socket 326. In other embodiments, the key notch 366 may extend along the whole length of the body 348 of the canister assembly 342 and the key groove 368 may extend along the whole length of the first recess 328 of the socket 326. In any of the embodiments described herein, the key notch 366 and groove 368 may be configured such that the canister assembly 342 may not be rotated/twisted within the socket 326 once the canister assembly 342 has been inserted into the socket 326.

One of the reasons it is important to ensure that the canister assembly 342 is inserted in the correct orientation is so that the first and second electronic connectors 356, 340 come into contact with each other. In one embodiment, the second electronic connector 340 may be an EPROM connector. The second electronic connector 340 may be disposed within the socket 326 as illustrated in FIG. 3B. The first electronic memory 356 may be disposed at the second end 346 of the canister assembly 342 as shown in FIG. 4B. The first and second electronic connectors 356, 340 may be thus disposed so that when the canister assembly 346 and the first recess 328 of the socket 326 are aligned properly, the first and second electronic connectors 356, 340 meet when the canister assembly 342 is fully inserted into the socket 326.

Figure 6A:
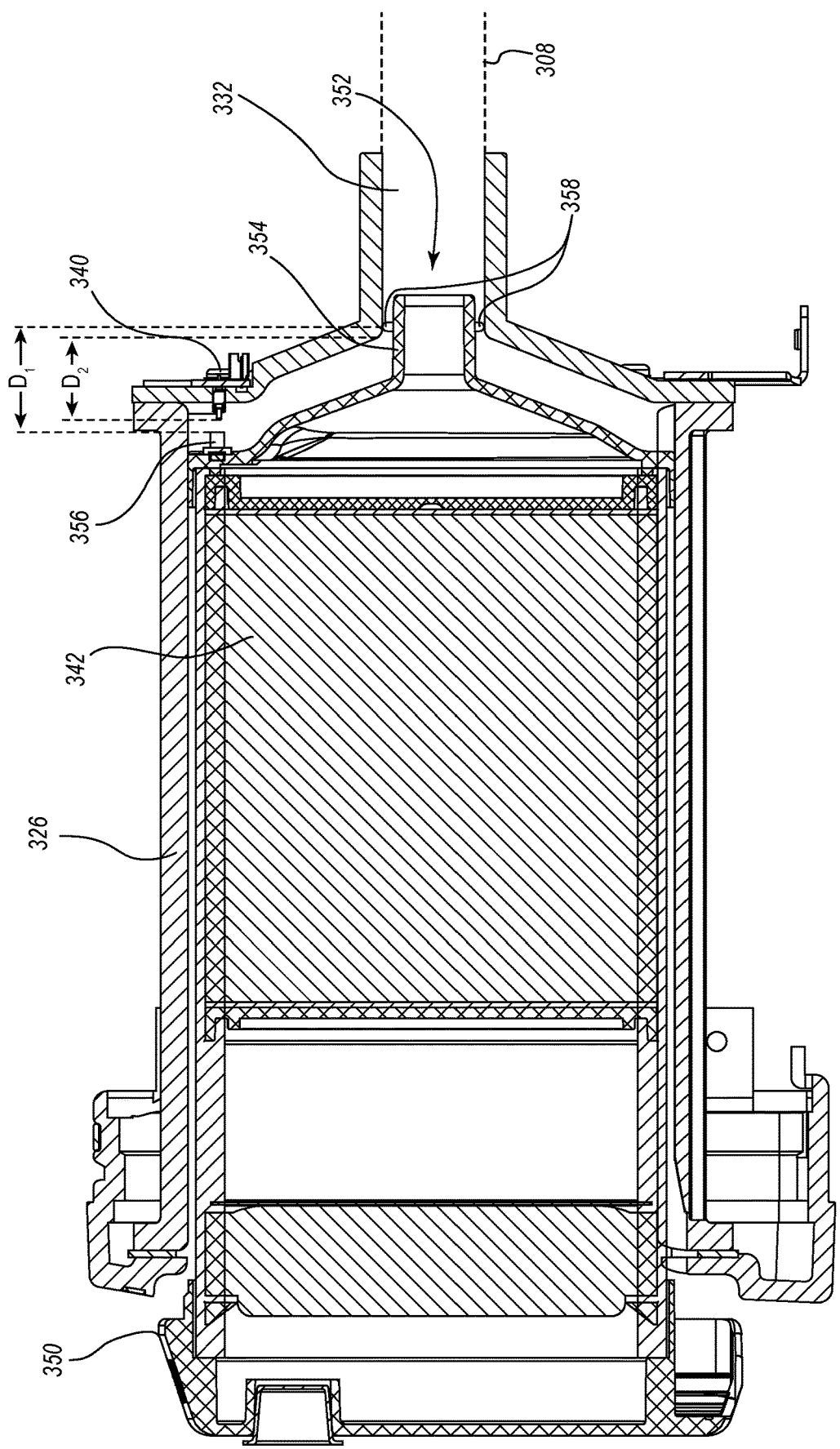
FIG. 6A illustrates a cross-sectional view of a filter canister assembly partially inserted into a socket.

In the illustrated embodiment of FIG. 4B, the first electronic connector 356 is disposed at an upper edge of the second end 346 of the canister assembly 342. This location corresponds to the location of the second electronic connector 340 disposed within the socket 326 as shown in FIG. 6A. Other embodiments may include first and second electronic connectors 356, 340 that are positioned at various locations on the second end 346 of the canister assembly 342 and in the socket 326. Any location is suitable so long as the first and second electronic connectors 356, 340 make contact when the canister assembly 342 is inserted into the socket 326.

Once the first and second electronic connectors 356, 340 contact each other, the electronic memory may relay information to a user or other components of the smoke evacuation system 342 regarding the filter. Such information may include, but is not limited to, the number of times the filter has been used, whether it is the correct filter, whether the filter is still functioning properly, how much life/filtration capacity is left in the filter, and so forth. This connection enables safe, reliable, and efficient use of filters that need to be periodically replaced. The electronic memory may also be used to signal that a filter has been inserted properly and activate the smoke evacuation system 300.

Figure 6B:
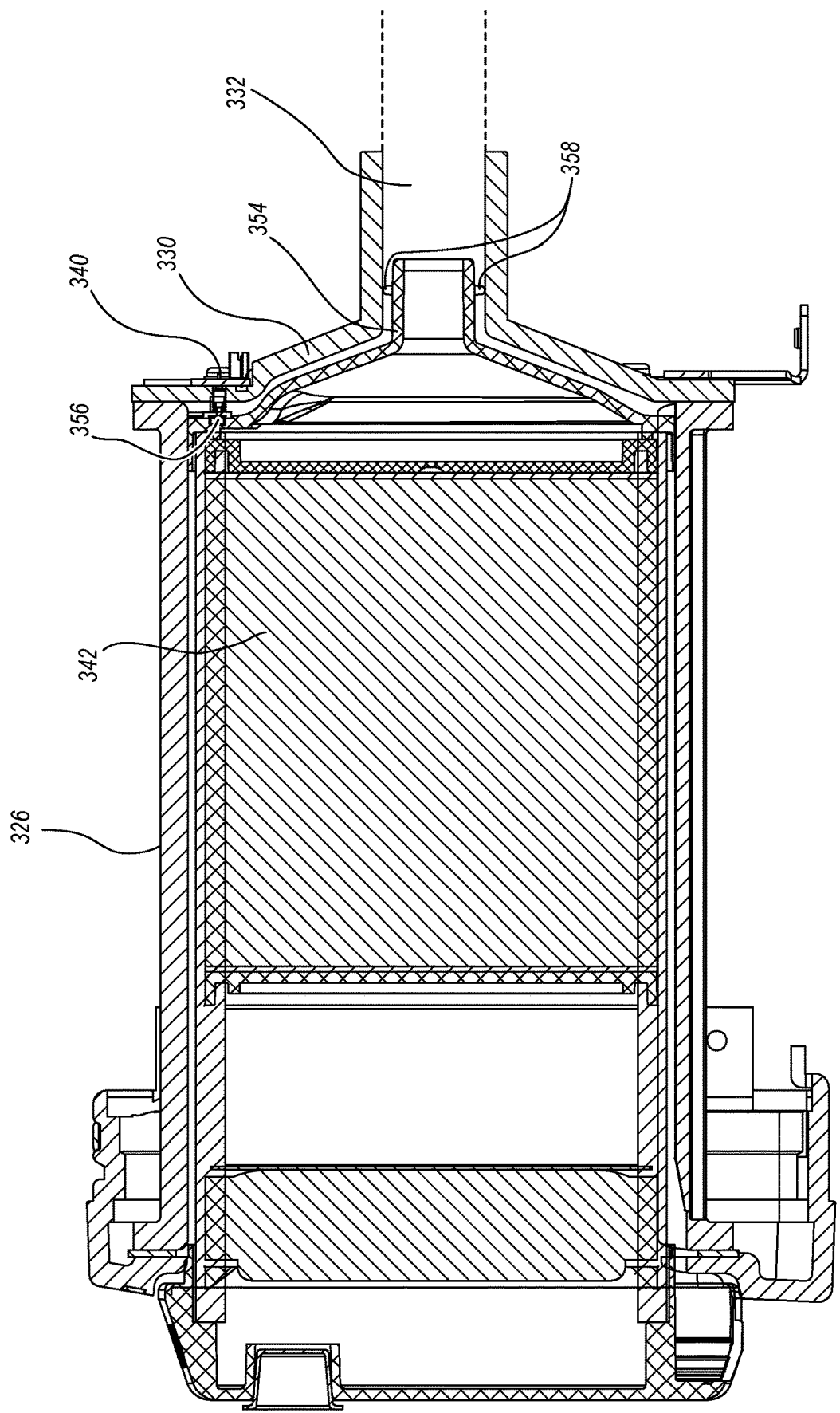
FIG. 6B illustrates a cross-sectional view of a filter canister assembly fully inserted into a socket.

FIGS. 6A and 6B illustrate an embodiment of canister assembly 342 inserted into socket 326. FIG. 6A illustrates canister assembly 342 partially inserted into the socket 326 and FIG. 6B illustrates a canister assembly 342 fully inserted into the socket 326. Referring to FIG. 6A, the canister assembly 342 is partially inserted into the socket 326 so that the connection nipple 354 is received by the second recess 332 of the socket 326. The seal 358 surrounding the connection nipple 354 makes contact with the inner surface of the second recess 332, creating a sealed path for a filtered gas exiting the canister assembly 342 at the canister outlet 352 to enter the airflow path 308 of the smoke evacuation system 300. In one embodiment, the seal 358 may be an O-ring. Other embodiments may include other seals 358.

The seal 358 makes contact with the inner walls of the second recess 332 to create a seal between the connection nipple 354 and the second recess 332 before the canister assembly 342 has been fully inserted into the socket 326. In this partially inserted configuration, the plate 350 does not contact the outer housing 320 of the smoke evacuation system 300 and the first and second electronic connectors 356, 340 do not make contact with one another.

FIG. 6B illustrates a canister assembly 342 fully inserted into the socket 326. When the canister assembly 342 is fully inserted into the socket 326, the seal 358 maintains a seal around the connection nipple 354 within the second recess 332. Additionally, when the canister assembly 342 has been fully inserted into the socket 326, the plate 350 makes contact with the outer housing 320 and/or the second end 346 of the canister assembly 342 abuts the transition surface 330 of the socket 326 so that the canister assembly 342 may not be inserted further. Furthermore, when the canister assembly 342 is fully inserted, the first and second electronic connectors 356, 340 contact one another. The electronic connection may then function as described above.

As discussed above, the electronic connection may activate or allow for activation of the smoke evacuation system 300 so that a suction begins drawing smoke into the filter 306 through the vacuum tube 112. In the embodiments illustrated herein, the seal creates an airtight boundary between the connection nipple 354 and the second recess 332 of the socket 326 before the first and second electronic connectors 356, 340 meet. In other words, the longitudinal distance D1 between the seal 358 and the first electronic connector 356 may be greater than the longitudinal distance D2 between the second recess 332 of the socket 326 and the second electronic connector 340. Longitudinal distances D1 and D2 are labeled in FIG. 6A.

Alternatively, the first electronic connector 356 may be disposed at the first end 344 of the filter canister 342 and the second electronic connector 340 may be disposed at or near the plate 350. In this configuration, the longitudinal distance between the seal 458 and the first electronic connector 356 may still be greater than the longitudinal distance between the second recess 332 of the socket 326 and the second electronic connector 340 so that a seal is created for smoke to pass through into the airflow path 308 before the first and second electronic connectors 356, 340 meet. It will be appreciated that both the first and second electronic connectors 356, 340 may be disposed at various locations on the filter canister 342 and in the socket 326 so long as the relationship between the longitudinal distances mentioned above remain the same.

These configurations ensure that the smoke evacuation system 300 will not be activated until the seal has been created so that filtered gas may not exit the canister outlet 352 until a closed path in communication with the airflow path 308 has been established. These configurations may prevent leakage of filtered gas exiting the canister assembly 342 at the canister outlet 352. These configurations may also ensure that the smoke evacuation system 300 does not begin drawing smoke through the filter 306 until the filter canister assembly 342 is inserted fully and properly into the socket 326.

Figure 7:
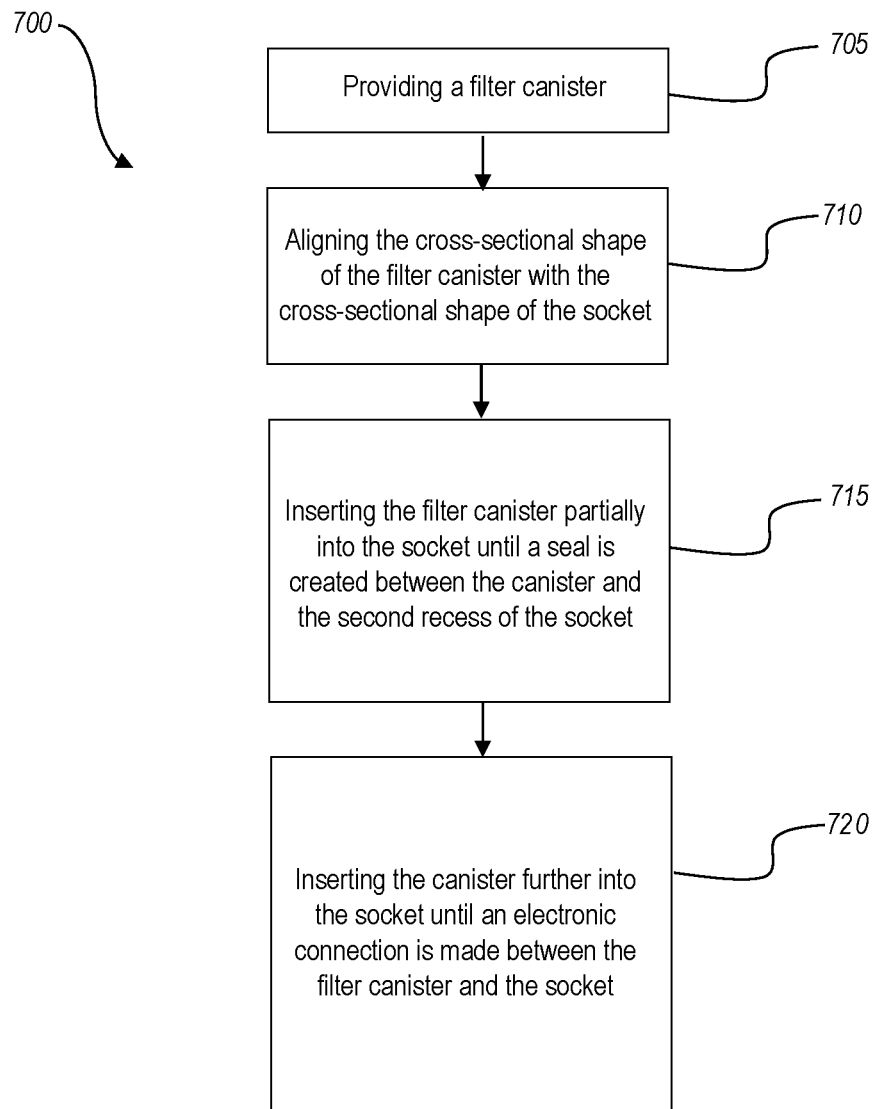
FIG. 7 illustrates a flow chart describing a method for connecting a canister to a smoke evacuation system.

FIG. 7 illustrates a method for connecting a filter canister to a smoke evacuation system 370. In a first step 372, a filter canister is provided. The filter canister may include a body disposed between first and second ends, a connection nipple disposed at the second end, a seal disposed around the connection nipple, a key notch, a cross-sectional shape, and a first electronic connector.

A second step 374 may include aligning the cross-sectional shape of the filter canister with a cross-sectional shape of the socket. The socket may comprise a first recess configured to receive the body of the filter canister, a second recess configured to receive the connection nipple, a transition surface connecting the first and second recesses, and a second electronic connector.

A third step 376 may include inserting the filter canister partially into the socket until the seal creates an airtight boundary between the connection nipple of the filter canister and the second recess of the socket. A fourth step 378 may include inserting the filter canister further into the socket until the second end of the filter canister makes contact with the transition surface of the socket and until the first and second electronic connectors come into contact with one another.

The method of inserting the filter canister described herein creates an airtight boundary between the connection nipple of the canister and the second recess of the socket before the electronic connection is made. In this way, the electronic memory, which may be configured to activate the smoke evacuation system, will not be connected until a sealed path that leads from the connection nipple to the airflow path of the smoke evacuation system has been established. This method may thus prevent filtered gas from leaking out of the filter canister before it is fully installed into the socket of the smoke evacuation system.

The present invention may be embodied in other specific forms without departing from its spirit or essential characteristics. The described embodiments are to be considered in all respects only as illustrative and not restrictive. Therefore, the scope of the invention is indicated by the appended claims rather than by the foregoing description. All changes, which come within the meaning and range of equivalency of the claims, are to be embraced within their scope.

What is claimed is:

1. A smoke evacuation system, comprising:
   a housing having a socket configured to receive a filter canister assembly at least partially therein, the socket comprising:
      an alignment feature; and
      an electronic connector; and
   a filter canister assembly configured to be at least partially inserted into the socket of the housing, the filter canister assembly comprising:
      an alignment feature, the alignment feature of the filter canister assembly corresponding to the alignment feature of the socket such that the filter canister assembly can be inserted into the socket when the alignment feature of the filter canister assembly is aligned with the alignment feature of the socket; and
      an electronic connector, the electronic connector of the filter canister assembly being configured to connect to the electronic connector of the socket when the alignment features of the socket and the filter canister assembly are aligned with one another and the filter canister assembly is fully inserted into the socket.

2. The smoke evacuation system of claim 1, wherein the alignment feature of the socket comprises a cross-sectional shape with only one line of symmetry.

3. The smoke evacuation system of claim 2, wherein the alignment feature of the filter canister assembly comprises a cross-sectional shape with only one line of symmetry, the cross-sectional shape of the filter canister assembly being substantially that same as the cross-sectional shape of the socket.

4. The smoke evacuation system of claim 3, wherein the cross-sectional shapes of the socket and the filter canister assembly comprise teardrop shapes.

5. The smoke evacuation system of claim 1, wherein the alignment feature of the socket comprises a key or a keyway and the alignment feature of the filter canister assembly comprises the other of a key or a keyway.

6. The smoke evacuation system of claim 1, wherein the socket comprises a first recess and a second recess.

7. The smoke evacuation system of claim 6, wherein the filter canister assembly comprises a body and a connection nipple, the body being configured for insertion at least partially into the first recess in the socket and the connection nipple being configured for insertion at least partially into the second recess in the socket.

8. The smoke evacuation system of claim 7, wherein the connection nipple comprises a seal configured to create an airtight boundary between the connection nipple and the second recess.

9. The smoke evacuation system of claim 8, wherein:
   the electronic connector of the socket is mounted therein a first distance away from the second recess; and
   the electronic connector of the filter canister assembly is mounted thereon a second distance away from the seal of the connection nipple, the second distance being greater than the first distance such that the seal creates an airtight boundary between the second recess and the connection nipple prior to connection of the electronic connectors when the filter canister assembly is inserted into the socket.

10. A smoke evacuation system, comprising:
    a housing having a socket configured to receive a filter canister assembly at least partially therein, the socket comprising:
       a cross-sectional shape with only one line of symmetry;
       a seal engagement surface; and
       an electronic connector, the electronic connector and the seal engagement surface being space apart a first distance; and
    a filter canister assembly configured to be at least partially inserted into the socket of the housing, the filter canister assembly comprising:
       a cross-sectional shape with only one line of symmetry, the cross-sectional shape of the filter canister assembly corresponding to the cross-sectional shape of the socket such that the filter canister assembly can be inserted into the socket in a single orientation;
       a seal disposed around an outer surface of the filter canister assembly and configured to engage the seal engagement surface to create an airtight boundary between the housing and the filter canister assembly; and
       an electronic connector, the electronic connector of the filter canister assembly and the seal being spaced apart a second distance that is greater than the first distance, such that when the cross-sectional shapes of the filter canister assembly and the socket are aligned and the filter canister assembly is inserted into the socket, the seal engages the seal engagement surface before the electronic connectors connect to one another.

11. The smoke evacuation system of claim 10, wherein the cross-sectional shapes of the socket and the filter canister assembly comprise teardrop or triangular shapes.

12. The smoke evacuation system of claim 10, wherein the cross-sectional shapes of the socket and the filter canister assembly comprises a mating key and keyway interface.

13. The smoke evacuation system of claim 10, wherein the electronic connectors of the socket and the filter canister assembly comprise erasable programmable read-only memory (EPROM) connectors.

14. The smoke evacuation system of claim 10, wherein:
the socket comprises a first recess and a second recess; and
the filter canister assembly comprises a body and a connection nipple, the body being configured for insertion into the first recess and the connection nipple being configured for insertion into the second recess.

15. The smoke evacuation system of claim 14, wherein the first recess comprises the seal engagement surface and the seal is disposed around the connection nipple.

16. The smoke evacuation system of claim 14, wherein the filter canister assembly further comprises an inlet port at an end thereof opposite to the connection nipple.

17. A method for connecting a filter in a smoke evacuation system, the method comprising:
providing a socket in the smoke evacuation system housing, the socket having one or more alignment features;
providing a filter canister assembly, the filter canister assembly having one or more alignment features that correspond to the one or more alignment features of the socket;
aligning the one or more alignment features of the filter canister assembly with the one or more alignment features of the socket;
creating an airtight boundary between the filter canister assembly and the socket; and
creating an electronic connection between the filter canister assembly and the socket.

18. The method of claim 17, wherein aligning the one or more alignment features of the filter canister assembly with the one or more alignment features of the socket aligns an electronic connector on the filter canister assembly with an electronic connector in the socket.

19. The method of claim 17, wherein creating an airtight boundary is completed prior to creating an electronic connection between the filter canister assembly and the socket.

20. The method of claim 17, wherein:
creating an airtight boundary between the filter canister assembly and the socket comprises inserting the filter canister assembly a first distance into the socket; and
creating an electronic connection between the filter canister assembly and the socket comprises inserting the filter canister assembly a second distance into the socket, the second distance being greater than the first distance.

* * * * *